US012649018B2

(12) United States Patent
Jakus

(10) Patent No.: US 12,649,018 B2
(45) Date of Patent: Jun. 9, 2026

(54) METHOD FOR FABRICATION OF ADDITIVELY MANUFACTURED, SELF-GELLING STRUCTURES AND THEIR USE

(71) Applicant: Dimension Inx Corp, Chicago, IL (US)

(72) Inventor: Adam E. Jakus, Chicago, IL (US)

(73) Assignee: DIMENSION INX CORP, Chicago, IL (US)

( * ) Notice: Subject to any disclaimer, the term of this patent is extended or adjusted under 35 U.S.C. 154(b) by 0 days.

(21) Appl. No.: 18/595,593

(22) Filed: Mar. 5, 2024

(65) Prior Publication Data

US 2024/0245836 A1     Jul. 25, 2024

Related U.S. Application Data

(62) Division of application No. 17/698,787, filed on Mar. 18, 2022, now Pat. No. 11,944,726.

(60) Provisional application No. 63/212,420, filed on Jun. 18, 2021.

(51) Int. Cl.

| | |
|---|---|
| *A61L 27/44* | (2006.01) |
| *A61L 31/12* | (2006.01) |
| *A61L 31/14* | (2006.01) |
| *B29C 64/112* | (2017.01) |
| *B33Y 10/00* | (2015.01) |
| *B33Y 40/10* | (2020.01) |
| *B33Y 40/20* | (2020.01) |
| *B33Y 70/10* | (2020.01) |
| *B33Y 80/00* | (2015.01) |
| *B82Y 5/00* | (2011.01) |

(52) U.S. Cl.
CPC ........... *A61L 31/145* (2013.01); *A61L 31/129* (2013.01); *A61L 31/146* (2013.01); *B29C 64/112* (2017.08); *B33Y 10/00* (2014.12); *B33Y 40/10* (2020.01); *B33Y 40/20* (2020.01); *B33Y 70/10* (2020.01); *B33Y 80/00* (2014.12); *A61L 2400/12* (2013.01); *B82Y 5/00* (2013.01)

(58) Field of Classification Search
CPC .... A61F 2/28; A61F 2/0007; A61L 2300/624; A61L 2300/802; A61L 27/44
See application file for complete search history.

(56) References Cited

U.S. PATENT DOCUMENTS

| | | | |
|---|---|---|---|
| 4,696,974 | A | 9/1987 | Sulc et al. |
| 9,327,448 | B2 | 5/2016 | Shah et al. |
| 10,236,528 | B2 | 3/2019 | Jakus et al. |
| 10,350,329 | B2 | 7/2019 | Shah et al. |
| 10,584,254 | B2 | 3/2020 | Shah et al. |
| 10,793,733 | B2 | 10/2020 | Shah et al. |
| 2014/0086898 | A1 | 3/2014 | Wallace et al. |
| 2017/0348458 | A1 | 12/2017 | Kesti et al. |
| 2018/0251649 | A1 | 9/2018 | Lewis et al. |
| 2018/0296343 | A1* | 10/2018 | Wei ........................ B33Y 50/00 |
| 2019/0060516 | A1 | 2/2019 | Martin et al. |
| 2019/0321291 | A1 | 10/2019 | Connolly et al. |
| 2019/0343989 | A1 | 11/2019 | Jakus et al. |
| 2020/0069846 | A1 | 3/2020 | Martin et al. |
| 2020/0254144 | A1 | 8/2020 | Horkay et al. |
| 2020/0353129 | A1 | 11/2020 | Jakus et al. |
| 2021/0260249 | A1 | 8/2021 | Alimperti et al. |

FOREIGN PATENT DOCUMENTS

| | | |
|---|---|---|
| CN | 112111073 A | 12/2020 |
| EP | 339035 B1 | 10/1992 |
| EP | 2814520 B1 | 11/2016 |
| WO | 9909149 A1 | 2/1999 |

OTHER PUBLICATIONS

Podstawczyk et al (3D printed stimuli-responsive magnetic nanoparticle embedded alginate methylcellulose hydrogel actuators, Additive Manufacturing 34, 2020 (Year: 2020).*
Wei, Xiangxia, et al. "Extrusion printing of a designed three-dimensional YBa2Cu3O7-x superconductor with milled precursor powder." Journal of Materials Chemistry C5.13 (2017): 3382-3389.
International Search Report and Written Opinion for PCT/US2022/021077 dated Jun. 14, 2022, 14 pages.
Extended European Search Report for EP22825483.5 dated Apr. 25, 2025, 10 pages.

* cited by examiner

*Primary Examiner* — Micah Paul Young
(74) *Attorney, Agent, or Firm* — Hahn Loeser & Parks LLP

(57) ABSTRACT

Disclosed are Self-Gelling materials and structures or materials or structures having one or more self-gelling components that overcome existing gel limitations due to hydrogel localization for medical applications by providing, for example, 1) microstructurally, or physically, anchored characteristics to help localize the gel, and the overall printed, or otherwise formed structure, giving structural form to the gel that allows the gel to be localized within the body, and even sutured in place, and mitigates gel migration and extends its residence time; 2) to provide an underlying 3D printed structure to help contain and support the gel after implantation; and more. Self-Gelling 3D printed structures may be further processed via milling to yield deconstructed scaffold micro-granules, with the composition and nano-/micro-structure of the original larger structure. Deconstructed scaffold micro-granules may be hydrated to form a micro-granule embedded gel network that can be injected, giving form to injectable gels.

9 Claims, 10 Drawing Sheets

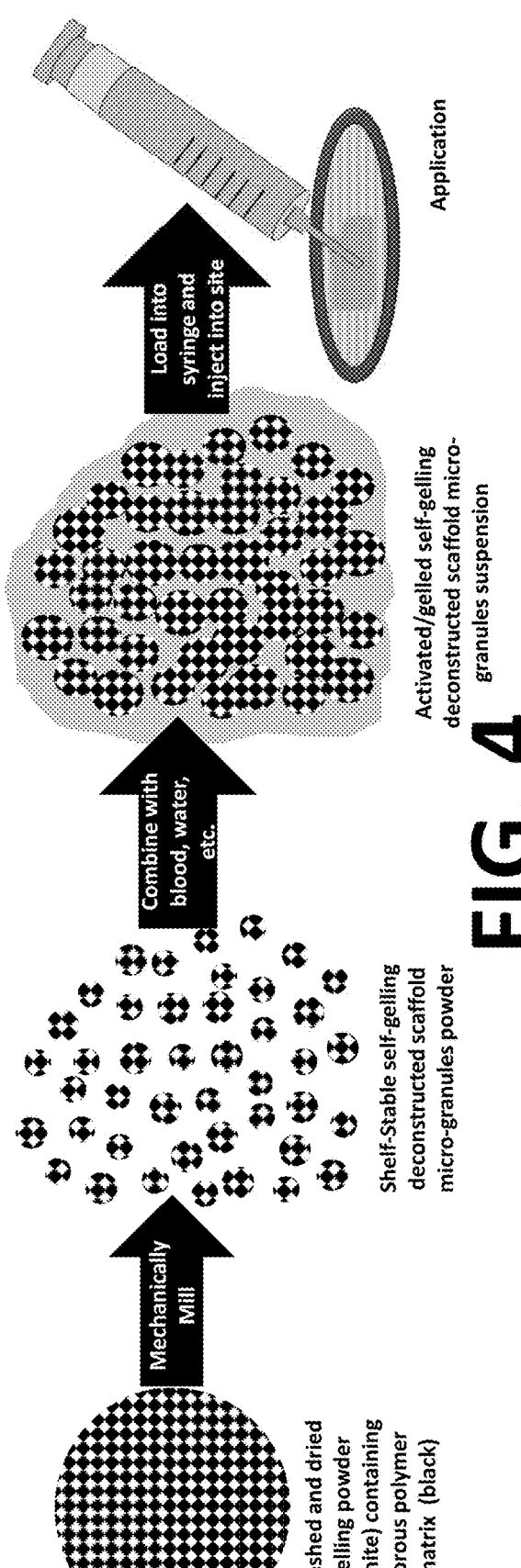

STEP 1
(STEP 3 From APPROACH 2 of FIG. 2A-2B)

Washed and dried gelling powder (white) containing porous polymer matrix (black)

Mechanically Mill

STEP 2
Self-Gelling deconstructed scaffold micro-granules representative of original larger structure Shelf-Stable self-gelling deconstructed scaffold micro-granules powder

Combine with blood, water, etc.

STEP 3
Self-Gelling deconstructed scaffold micro-granules gel and expand into a microstructurally gel-anchored, flowable suspension Activated/gelled self-gelling deconstructed scaffold micro-granules suspension

Load into syringe and inject into site

STEP 4
Inject into or onto tissue, organ, or wound site

Application

METHOD FOR FABRICATION OF ADDITIVELY MANUFACTURED, SELF-GELLING STRUCTURES AND THEIR USE

This patent application is a divisional of, and claims priority to and benefit of, U.S. application Ser. No. 17/698,787, filed Mar. 18, 2022, which claims priority to and benefit of U.S. Provisional Application No. 63/212,420, filed Jun. 18, 2021, all of which are incorporated herein by reference.

BACKGROUND

This disclosure relates to hydrogel localization and stabilization.

Hydrogels are useful base materials for medical and other applications, including, for example, for tissue healing and regeneration, drug delivery, cell delivery, encapsulation of implantable devices and bioelectronics. They are physically similar to the natural matrix and make up of the human body—a loose, nano network containing hydrogen- or electrostatically-bound water-based media (i.e., much of the human body is gel-like). Because of the physical similarities to biological systems, hydrogels have numerous medical applications, including but not limited to: tissue repair, drug delivery, gene delivery, cell delivery, and inflammation reduction. However, hydrogels intended for medical use, particularly those designed for fixed placement in the body and/or injection, suffer from numerous drawbacks, which include that they 1) are difficult to localize (gels will easily move and become delocalized as a result of mechanical stress after implantation) and 2) tend to break, tear, disperse, or fall apart due to movement resulting from the inability to be localized. These technical deficiencies greatly limit the effectiveness of medical hydrogels across applications. Additionally, hydrogels must often be prepared onsite, in the operating room, and/or in the clinician's office immediately prior to use—adding procedure time and cost as well as increasing the likelihood for preparation and application mistakes.

SUMMARY

The materials and structures having one or more self-gelling components as defined in this invention in various embodiments offer improved performance over existing, non-microstructurally anchored gels because, for example, 1) the microstructurally, or physically, anchored characteristics help localize the gel, and the overall printed, or otherwise formed structure, give structural form to the gel—allowing the gel to be localized within the body, and even sutured in place—mitigating gel migration, increasing resistance to mechanical forces, and extending its residence time; 2) the underlying 3D printed scaffold or deconstructed 3D printed scaffold particle materials' designed macro-, and inherent micro- and nanostructure structures help contain and support the gel after implantation or injection; and/or 3) the pre-activated Gelling Powder containing 3D-printed scaffold material is shelf-stable and can be cut, trimmed, compressed, delivered via cannula, etc., for example, prior to hydration—allowing it be placed and hydrated with surrounded blood, media, plasma, etc. upon implantation or injection—greatly increasing the device's ability to integrate and heal surrounding tissue. As used herein, one or more self-gelling components, or one or more self-gelling powder components, refers to one or more of the same self-gelling component and/or one or more of different self-gelling components. The presently disclosed materials having one or more self-gelling components are distinct from injectable hydrogels as well as implanted 3D printed hydrogels, which are much slower to absorb surrounding biological components because they are already hydrated. Additionally, the underlying, nano- and micro-porous polymer mesh, in the form of a 3D printed structure or deconstructed 3D printed structure, help maintain implant form or injectable volume, respectively, improving localization better than polymer or composite meshes that have had gels added to them prior to implantation, where the gel component is not anchored within the nano-/micro-structure of the polymer network and is instead just loosely encapsulating the mesh.

A Gelling Powder containing material, or structure, is disclosed, where the Gelling Powder is essentially anhydrous, and is intended to be gelled after generating, or forming, a 3D-printed structure and/or after fabrication of deconstructed granules. In other words, the Gelling Powder is gelled only upon being activated in a post-processing treatment, as further disclosed below. The Gelling Powder containing material, and underlying matrix, or mesh, structure, further expands upon hydration, that is the gelation, or upon being otherwise activated, because of the embedded Gelling Powder expanding and pushing against a polymer microporous matrix, or mesh, network. Because the Gelling Powder is essentially anhydrous, gelling powder comprising deconstructed scaffold micro-granules may additionally be achieved by milling of extruded or otherwise formed material derived from the Gelling Powder comprising ink for further incorporation into a subsequent ink composition, or a deconstructed scaffold micro-granule containing Gelling Powder (referred to herein more generally as "Deconstructed Scaffold Gelling Granules"). The micro-granules, themselves, are discrete particles comprised of discrete particles of gelling powder embedded within a porous biodegradable polymer matrix or, in other words, the deconstructed scaffold micro-granule is comprised of the biodegradable polymer matrix with embedded gelling particle. Granule is understood as being larger than a powder particle and the Deconstructed Gelling Granule is a micro-granule produced from a deconstructed scaffold that otherwise contains gelling powder.

The present disclosure also includes a 3D printed structure having one or more self-gelling components, the 3D printed structure comprising a porous polymer or polymer-composite matrix, or mesh, structure encapsulating, or integrating, a dry gelling powder and/or a deconstructed scaffold micro-granule (i.e., Gelling Powder and/or Deconstructed Scaffold Gelling Granule) that is shelf-stable in dry form wherein the gelling powder component of the structure is configured to gel when contacted with an aqueous solution. The structure may additionally comprise micro and/or nano particles embedded within the porous polymer matrix, or mesh, structure in dry form, which become further internally saturated and encapsulated by gel after the structure is exposed to an aqueous solution. The micro and/or nano particles may be one or more of electrically conductive materials, ceramic materials, metallic materials, and biologically derived materials. The structure may further additionally comprise drugs, small molecules, RNA, and/or DNA and their derivatives. The polymer matrix, or mesh, structure may be a biocompatible polymer matrix, or mesh, structure. The dry gelling powder and/or the deconstructed scaffold micro-granule (i.e., Gelling Powder and/or Deconstructed Scaffold Gelling Granule) is disposed within the porous microstructure of the biocompatible polymer matrix, or mesh, structure. In examples, the dry gelling powder containing or micro-granule containing 3D printed structures (containing either Gelling Powders and/or Deconstructed Scaffold Gelling Granules) may be water washed or washed in an aqueous solution, where the gelling powders undergo gelation to form a voluminous gel and become microstructurally, or physically, anchored within the interconnected nano- and micro-porosity of the porous biocompatible polymer matrix, or mesh, structure. As referred to herein, nano- and micro-porosity refers to porous properties that range from a nano-scale to a micro-scale. In such examples herein, the porosity may be on both the nano-scale and the micro-scale. In such examples herein, the porosity may be on the nano-scale only. In such examples herein, the porosity may be on a micro-scale only. The matrix, or mesh, structure, as well as the Deconstructed Scaffold Gelling Granules are very porous. The pore sizes of these materials are of the said nano- and micro-porosity, or alternatives, as noted here. It is noted, however, that the pores of the porous biocompatible polymer matrix are not larger than the Deconstructed Scaffold Gelling Granules themselves. In particular examples, the pores of the porous biocompatible polymer matrix are not larger than 20 μm in size.

Also described is an ink composition for extrusion-based 3D printing of a 3D printed structure having one or more self-gelling powder components, the ink composition comprises a solvent-based biocompatible polymer comprising and maintaining a dry gelling powder that is encapsulated, or integrated, within the biocompatible polymer that is configured after printing to be washed in alcohol, remain shelf-stable in a dry form upon drying, and gel upon hydration in an aqueous solution. In examples, the ink composition is not and does not comprise a hydrogel. In examples, the dry gelling powder has an average particle size of less than 100 μm. In examples, the dry gelling powder component is used in combination with one or more electrically conductive materials, ceramic materials, metallic materials, or biologically derived materials (such as, for example, proteins, peptides, extracellular matrix, etc.). These other materials may also be in powder form but may be different than or distinct from the dry gelling powder and may be provided in addition to the dry gelling powders. These particles may be the above-mentioned micro and/or nano particles. The micro and/or nano particles may be any composition that does not dissolve in the primary solvent used in the ink, dichloromethane, or the alcohol solutions utilized during the washing step. In an example, an additional powder component comprising one or more of nano-scale and micro-scale materials that may be one or more of electrically conductive materials, ceramic materials, metallic materials, and biologically derived materials are suspended in the solvent-based polymer extrusion.

Also described is a method of forming a structure having one or more self-gelling components comprising the steps of:

combining a solvent-based polymer with a dried gelling powder to form an ink and extruding the ink to form a structure having an interconnected nano- and micro-porous polymer matrix, or mesh, with embedded gelling powder;

washing the structure having the nano- and micro-porous polymer matrix, or mesh, with embedded gelling powder through a series of alcohol solution and water washes to remove residual solvents;

activating and gelling the dried gelling powder in the step of washing where the dried gelling powder absorbs water and transforms into a gel which fills, exudes from, and encapsulates the microporous polymer matrix, or mesh, structure;

drying the gel containing an encapsulated microporous polymer matrix, or mesh, into a shelf-stable structure and in a dry form; and hydrating the shelf-stable structure in an aqueous based solution.

The solvent-based polymer may be a solvent-based biocompatible polymer. The dry microporous polymer matrix, or mesh, with embedded gelling powder may additionally be mechanically milled to produce gelling powder containing deconstructed scaffold micro-granules or, in other words, a Deconstructed Scaffold Gelling Granule. The step of hydrating may be the step of implanting the shelf-stable structure into a patient. The method may further comprise the steps of:

creating an interconnected solid-gel suspension by hydrating the Deconstructed Scaffold Gelling Granule connected by and suspended within a gel network (micro-granular embedded gel) by hydrating the structure having a microporous polymer matrix with an embedded dried gelling powder; and injecting the interconnected solid-gel suspension through a syringe forming a distinct structure comprising a continuously connected hydrogel anchored within and surround discrete units of nano- and micro-porous biocompatible polymer particles before the step of washing wherein the gel is microstructurally, or physically, anchored within the nano- and micro-porous biocompatible polymer particles after the step of hydrating.

The present disclosure describes another 3D printed structure having one or more self-gelling components. This 3D-printed structure comprises a polymer matrix, or mesh, structure encapsulating, or integrating, an anhydrous washed and absorbent dry gelling powder of discrete, dehydrated, particles that are lyophilized and are configured to gel in an aqueous based solution. The dry gelling powder may be configured to be anchored within a microstructure of the polymer matrix, or mesh, structure upon gelation. In other words, the dry gelling powder is embedded within the microstructure of the polymer matrix, or mesh, and once the gelling powder is exposed to water, and thereafter gels, the resulting gel is anchored to the position of the originating dry gelling powder particle, which is within the nano- and micro-porous non-gelling polymer microstructure. The gel encapsulates and surrounds the polymer microstructure, but also permeates and is anchored within it. The self-gelling 3D printed structure may further comprise micro and/or nano particles configured to be embedded within the microporous polymer matrix, or mesh, structure by being encapsulated in a solid-gel suspension encapsulated, or integrated, within the polymer matrix, or mesh, structure upon gelation. The polymer matrix, or mesh, structure may be a biocompatible polymer matrix, or mesh, structure. In examples, the ink composition itself is not and does not comprise a gel.

The micro and/or nano particles may be embedded within the porous polymer matrix, or mesh, similar to the gelling powder. Upon hydration the gelling powder turns into gel and expands, which fills and encompasses the porous polymer matrix, or mesh, as well as encompassing the surrounding micro and/or nano particles. The length scale of the micro and/or nano particles is such that the development and expansion of the gel powder upon hydration actually moves/pushes the micro and/or nano particles through the porous polymer network. In one example, the nanoparticles move with the hydrated gel while the microparticles do not move or do not significantly move with the expanding gel.

The present disclosure describes another ink composition for printing a 3D printed structure. The ink composition comprises a solvent-based polymer encapsulating, or integrating, an anhydrous gelling powder of discrete particles wherein the gelling powder is configured to gel in an aqueous based solution after extrusion. In other words, the gelling powder is extruded with the ink and does not gel until after extrusion, or a 3D printed structure is formed. The gelling powder is extruded with the ink and does not gel until after extrusion because it does not gel until being exposed to an aqueous environment. Thereafter, the 3D printed structure may be exposed to an aqueous based solution and the gelling powder gels. In other words, the gelling powder containing ink does not gel during extrusion, after extrusion, or after formation of a 3D printed structure until the 3D printed structure is exposed to an aqueous environment. The ink composition may further comprise micro and/or nano particles configured to be embedded within the microporous polymer matrix, or mesh, with embedded gelling powder structure. The solvent-based polymer is a solvent-based biocompatible polymer. In examples, the ink composition is not and does not comprise a gel. Further, in examples, the 3D printed structure is not and does not comprise a gel. In examples, the dry gelling powder has an average particle size of less than 100 m. In some examples, the dry gelling powder component is used in combination with one or more electrically conductive materials, ceramic materials, metallic materials, drugs, synthetic chemistries, or biologically derived materials.

Also described is a method of forming a polymer structure with one or more self-gelling components comprising the steps of:

combining a solvent-based microporous polymer with a dried gelling powder to form an ink and extruding the ink to form a microporous polymer with embedded gelling powder structure;

washing the microporous polymer with embedded gelling powder structure in a non-aqueous solvent or anhydrous wash to prevent pre-gelling;

drying the washed microporous polymer with embedded gelling powder structure to form a dry shelf-stable structure; and activating and gelling the gelling powder component of the dry shelf-stable structure by hydrating the dry shelf-stable structure in an aqueous based solution where the gelling of the dried gelling powder component absorbs water or a primary aqueous solution (e.g., including but not limited to water, blood, cell suspension, biological plasma, drug containing solutions, or the like), gels, and expands the microporous polymer matrix, or mesh, component of the dry shelf-stable structure The solvent-based polymer may be a solvent-based biocompatible polymer. The dry microporous polymer matrix, or mesh, with embedded gelling powder structure may additionally be mechanically milled to produce Deconstructed Scaffold Gelling Granule. The step of hydrating may be the step of implanting the shelf-stable structure having the Gelling Powder and/or the Deconstructed Scaffold Gelling Granule into a patient. The step of implanting the dried shelf-stable structure or material may occur before the step of activation or gelling. The Deconstructed Scaffold Gelling Granules may be further formed by a step of mixing, or combining, distinct deconstructed scaffold micro-granules. For example, a quantity of Hyaluronic Acid self-gelling micro-granules may be dry mixed with a quantity of gelatin or collagen self-gelling micro-granules, also in dry form. Hydration would occur after dry mixing. The method may further comprise the steps of:

creating a micro-granule embedded gel suspension by hydrating the gelling powder containing micro-scaffold particles (i.e., the structure having a microporous polymer with an embedded gelling powder); and injecting the solid-gel suspension through a syringe forming a distinct structure comprising a continuous hydrogel anchored within and surround distinct units of nano- and micro-porous biocompatible polymer particles before the step of washing wherein the gel is microstructurally, or physically, anchored within the nano- and micro-porous biocompatible polymer particles after the step of hydrating.

In examples, the micro and nano particles are embedded within the microporous polymer. The nano particles may be or may comprise a metal, a ceramic, a drug, RNA, DNA, bioactive factor, or other biologically relevant material and the micro particles may be or may comprise a metal, a ceramic, a drug, RNA, DNA, bioactive factor, or other biologically relevant material different from the nano particles. In one example, the nano particles are metal and the micro particles are ceramic and vice versa. In some examples, the above methods may further comprise a step of implanting the dry shelf-stable material before the step of activation or gelling.

The foregoing and other objects, features, and advantages of the examples will be apparent from the following more detailed descriptions of particular examples as illustrated in the accompanying drawings wherein like reference numbers represent like parts of the examples.

BRIEF DESCRIPTION OF THE DRAWINGS

Reference is made to the accompanying drawings in which particular examples and further benefits of the examples are illustrated as described in more detail in the description below, in which:

FIG. 4 is a flow diagram of an additional approach (referred to herein as APPROACH 3) of Dried Gelling Powder Structures, or Gelling Powder containing structures, such as extruded fibers, that undergo additional processing (e.g., mechanically milling) to yield deconstructed scaffold micro-granules or, in other words, Deconstructed Scaffold Gelling Granules. Such a collection of deconstructed scaffold micro-granules or, in other words, Deconstructed Scaffold Gelling Granules would be shelf-stable in dry form, but could be hydrated (see below), resulting in gelling of the powders contained within the particles' polymer matrices lubricating the particles, and create an interconnected network of discrete micro-granules connected by and suspended within a gel network, as referred to herein as a solid-gel suspension, that is capable of injection through a syringe. Such a hydrated material could be 3D-printed into an additionally distinct material, or structure, (one comprised of non-continuous distinct units of nano- and microporous biocompatible polymer particles, connected by a gel network characterized by microstructured anchored "points" within each biocompatible polymer microparticle), in accordance with an example of the disclosure.

DETAILED DESCRIPTION

Figure 1B:
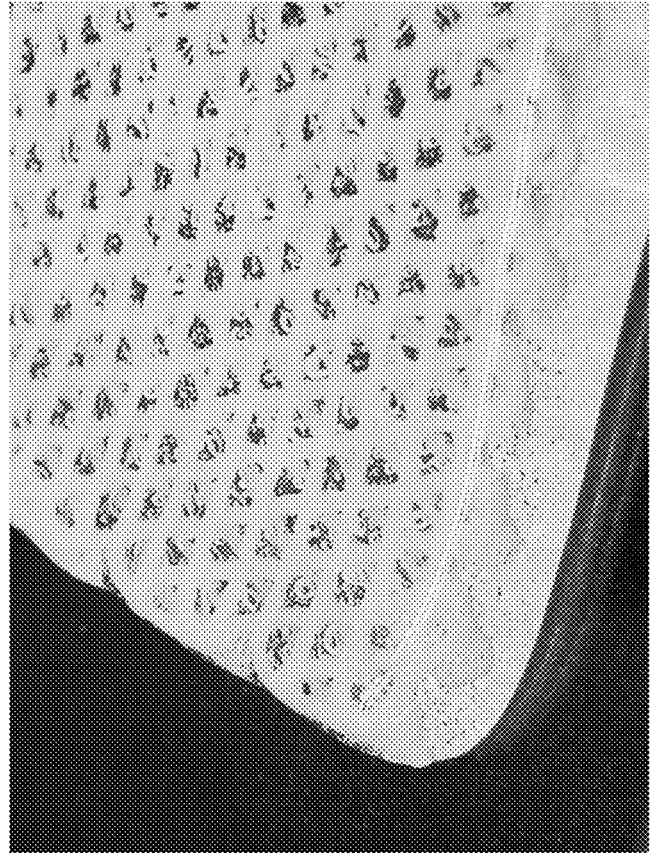
FIG. 1B is an image of a product of the present disclosure having a gelling powder added to a 3D printing ink composition and that has undergone activation, or gelation, (after activation, or gelation), such as a post-printing, or post-processing, rehydration process to form a gel that exudes from and surrounds the microporous polymer matrix, or mesh, and is microstructurally, or physically, anchored (within a polymer matrix, or mesh, framework), in accordance with an example of the disclosure.
Figure 1A:
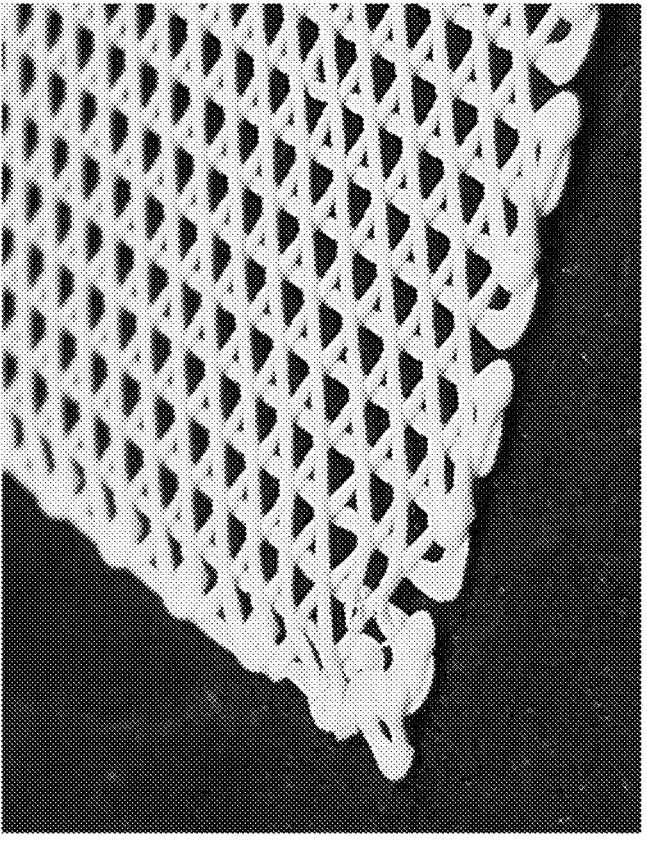
FIG. 1A is an image of a product of the present disclosure having a gelling powder added to a 3D printed ink composition of the product before formation and where the product is illustrated before activation, or gelation, in accordance with an example of the disclosure.

The self-gelling materials and structures defined in this invention in various embodiments offer improved performance over existing gel limitations because, for example, 1) the microstructurally, or physically, anchored characteristics help localize the gel, and the overall printed, or otherwise formed structure, give structural form to the gel—allowing the gel to be localized within the body, and even sutured in place—mitigating gel migration and extending its residence time; 2) the underlying 3D printed structure helps contain and support the gel after implantation; and/or 3) the dried Gelling Powder and/or the dried Deconstructed Scaffold Gelling Granule containing material is shelf-stable and can be cut, trimmed, compressed, delivered via cannula, etc., for example, prior to hydration—allowing it be placed and hydrated with surrounding blood, media, plasma, etc. upon implantation—greatly increasing the device's ability to integrate and heal surrounding tissue. The presently disclosed structures having one or more self-gelling components are distinct from injection of an already hydrated gel, which is much slower to absorb surrounding biological components because it is already hydrated. Additionally, the underlying polymer mesh structures help maintain implant form and localization better than a polymer mesh that has a gel added to it prior to implantation, where the gel is not microstructurally, or physically, anchored within the microstructure of the polymer network and is instead just loosely encapsulating it. FIG. 1A illustrates a material made from an ink comprising a gelling powder, where the material is in a dry shelf-stable state before activation, or gelation. FIG. 1B illustrates an activated self-gelled material made from a gelling powder comprising ink.

In the briefest form, this invention: Solves the problem of hydrogel localization for medical applications (allowing existing gels to be more effective). Specifically, "self-gelling" structure is defined herein as a structure, scaffold, or material that may be implanted/installed/placed as a dry, structured object into a wound, or body, or an environment as an implant and upon being exposed to the moisture of the body, or installed environment, at least a portion of which is activated to form a gel encapsulating and anchored within a defined microporous polymer structure. In other words, "self-gelling." The Gelling Powder within the polymer matrix, or mesh, "activates" by essentially soaking up water (and whatever is in the water such as, for example, blood cells), sometimes soaking up to 5-times its own weight or more. The absorption results in a very large volume change and effective transformation of dry solid gelling powder particles into expansive, wet hydrogel that saturates the nano- and micro-pores of the polymer (i.e., polyester matrix, or mesh) and ends up exuding beyond the boundaries of the polymer component, encapsulating polymer material and generally encapsulating the larger 3D printed structure.

In this "Activated State" the form of the 3D printed polymer material remains in its original configuration (although expanded slightly as a result of the gel expansion pushing on the polymer pore walls from the inside out as gel was forming), acting as a polymeric reinforcement to the gel.

Three specific application areas, to be used as examples, illustrates the benefits of the approach of the present disclosure are as follows:

Example 1

Biological joint (osteochondral) repair with 3D-printed hyaluronic acid structures having one or more self-gelling components. In this example, hyaluronic acid (HyAc) is frequently used for treating damaged or degraded joints (trauma, arthritis, side effect of surgery, etc.), as it is a naturally present material in cartilaginous joint tissues. For these treatments, HyAc is typically employed as injectable gel or added to an existing implant device and implanted. Although HyAc is compositionally relevant to treating joint disorders, HyAc gel injections have limited and short-lived impact due the fact that HyAc gel migrates away from the initial injection site as a result of normal biological movement. This migration also results in the HyAc gel physically breaking down and not adequately incorporating into or integrating with the surrounding tissues. This problem is slightly mitigated if the gel is injected into an existing porous structure which is subsequently implanted; however, the gel is not well integrated with the porous implant structure and will also begin to migrate away from the site because of movement. Additionally, both of these existing approaches require the gel to be a hydrated gel immediately prior to implant, limiting the amount of surrounding blood and biological media that can be absorbed by the injection or implant. With the current invention, a designer structure (whatever shape and form factor is needed) could be deployed to the desired site via standard or minimally invasive or cannulated processes and sutured to surrounding tissues—fixing it into place while the structure is absorbing surrounding blood, cells, etc., swelling as a result, and further fixing it into place. The resulting gel within the structure is microstructurally, or physically, anchored with the polymer mesh network, helping to keep it localized even during movement—thus extending its residency time and therapeutic effect.

Example 2

Injectable gels to treat damaged tissues or organs (i.e., cardiac tissue after infarction) Similar to the previous example, a number of conditions result in surface or subsurface damage to tissues and organs—one example being cardiac infarction, whereby cardiac tissue dies. Emerging methods to treat this include injecting hydrogels with drugs, cells, etc. directly onto the damaged tissue. However, due to the surface nature of the defect as well as the dynamic nature of the organ, the gel does not stay localized for an extended period of time, limiting its therapeutic potential. For example, a sheet of material having one or more self-gelling components could be delivered via canula to the heart and fixed (via surgical glue or fine suture) to/around the injury site. The implant was in the form of the structure having a self-gel during this process, and the resulting gel would be anchored within the structural, highly porous polymeric microstructure of the structure—keeping the implant localized to the desired site.

Example 3

In instances where injectables are still required (minimally invasive procedures where larger implants can't be used), the micro-scaffold approach (Approach 3 described below), could be used in place of directly injecting hydrogel. Although not as effective at localizing the gel as a larger structure would be, the existence of the microparticles and integration with the exuded gels, would help retain the form and residence time of the injection. One example would be for treating subsurface spinal cord injuries, whereby an injection of micro-scaffold particles into the injury site would result in self-gelling (expanding) therapeutic filler that is anchored to the site in part due to the connection between the gel and the microporous structure of the polymer microparticles.

Examples of the present disclosure may be relied on as a unique extension of, or improvement to, the ink compositions and/or scaffold materials of U.S. Pat. No. 10,584,254 entitled INK COMPOSITIONS FOR THREE-DIMENSIONAL PRINTING AND METHODS OF FORMING OBJECTS USING THE INK COMPOSITIONS, filed 14 Nov. 2016, which is herein incorporated by reference in its entirety (hereinafter referred to as the "'254 patent"). The '254 patent sets forth a (laminarly-extrudable, at room-temperature, without chemical or thermal reaction) 3D-printable "ink" created from a series of solvents, biocompatible polymer, and particles/powders. This "ink" can be 3D-printed into a variety of form factors and is also amenable to other manufacturing methods (such as, for example, fiber forming, textiles, weaving, casting, etc.). While the basic ink composition approach may rely on compositions of the above '254 patent, the present disclosure sets forth a post-processable material, a process, a means of use, and/or features distinct from the basic ink composition described in the '254 patent. Specifically, the present disclosure sets forth a Gelling Powder and self-gelling technique that is structurally supported by the ink composition and/or scaffold of the '254 patent while remaining localized, as shown to be a deficiency of the prior art. It is appreciated herein that while the '254 patent is relied on as an example of an ink composition and/or structures, or scaffolds, the self-gelling techniques and the Gelling Powder of the present disclosure may be relied on as an improvement to other ink compositions and/or structures, or scaffolds, as set forth below.

The Powder and the Ink

In the instance of the current invention, an ink, such as that disclosed by the '254 patent, may comprise one or more of the post-forming powders that is a dry (essentially moisture free), hygroscopic, and highly moisture (water) absorbent material (hereinafter, "Gelling Powder"), that undergoes substantial swelling when exposed to moisture. The Gelling Powder must not be substantially soluble or is non-soluble in non-polar solvents, such as alcohols or dichloromethanes. If the intended use of the ink is for extrusion-based 3D printing, such as that disclosed by the '254 patent, it is preferred that the Gelling Powder have an average particles size of less than 100 μm to allow for extrusion from a fine tip nozzle and deposition of material.

The Gelling Powder may be synthetic (e.g., Polyethylene glycol, polyethylene oxide, or their variants), natural (gelatin, cellulose, chitosan, alginates, "gums", hyaluronic acid, other polysaccharides), zeolites, naturally derived (hyaluronic acid and previously mentioned materials from bacterial or fungal fermentation) materials, synthetically derived natural materials (synthetically produced collagen), silicates, silicon-based polymers or combinations thereof. In some examples, the Gelling Powder is capable of retaining via H—H interactions (Hydrogen bonding) or electrostatic interactions significant volumes of water. Significant may mean equal to or greater than the dry mass of the Gelling Powder. For example, 1 gram of dry Gelling Powder should be able to retain at least 1 gram of water or other aqueous based solution. The Gelling Powder may be chemically functionalized (small molecules, drugs, proteins, peptides, nanoparticles, acid group, base group, etc.) prior to use in ink synthesis, provided that the functionalization does not impart solubility in a non-aqueous solvent, such as alcohol or dichloromethane. The Gelling Powder can exhibit a wide range of average molecular weights, molecular numbers, polydispersities, etc. Molecular weights may range from 500 to 5,000,000 Daltons in most examples.

A typical ink, relied on to be used in combination with the Gelling Powder, is comprised of a tri-solvent mixture of evaporant (such as for example dichloromethane), surfactant (such as for example 2-butoxyethanol), plasticizer, and polymer. The polymer may be a non-biocompatible polymer such as, for example, one or more of polystyrene, polyvinyl alcohol, etc. The polymer may additionally, or alternatively, be a biocompatible polymer such as, for example, one or more of poly(lactide-co-glycolide) (PLG), polylactide (PLA), polycaprolactone, polyglycolide, etc. The ink of the present disclosure may additionally, or alternatively, be used with cyclodextrins to adjust the solubility of the ink composition. The tri-solvent mixture and polymer and, more specifically, the biocompatible polymer may be generally the same as previously described in the '254 patent. A polymer may be added to and dissolved in the evaporant (dissolving slowly under ambient conditions). In one specific example, 1 g of polymer is used for every 2-10 g of evaporant. The evaporant amount may be changed depending on the desired viscosity of the final ink. The surfactant and plasticizer are added to the evaporant/dissolved polymer. The amount of surfactant relative to the evaporant may vary depending on the desired final properties of the ink and the nature of the powder being used.

In the present disclosure, the ink is combined with the Gelling Powder or the ink comprises the Gelling Powder. The combination of the Gelling Powder and the ink is a single integrated material. In one example, the powder component makes up 50-80 vol. % (solids content, polymer+powder). All of the powder components of the resulting ink can be the Gelling Powder(s), including multiple distinct Gelling Powders or the powder component can be partially comprised of Gelling Powders and partially comprised of non-gelling powders compatible with the underlying ink composition (does not dissolve in dichloromethane or similar non-polar solvents). For example, the ink may contain 35 vol. % Hyaluronic Acid (AKA: sodium hyaluronate—the Gelling powder) and 35 vol. % bioceramic (e.g., calcium phosphate, such as bioceramic). The combination of the ink and the powder should be substantially free of water or other aqueous-based fluids. The inks will rapidly dry and solidify when exposed to air. The molecular weight of the gelling powder can range from 10,000 kDa to 10,000,000 kDa. In specific examples, the Gelling Powder is added last. The ink is physically mixed until it is homogenous at which point it is ready to 3D print via room-temperature extrusion. The resulting 3D printed structure comprise the polymer (which exists as a nano- and micro-porous matrix, in addition to the larger 3D printed macro form), the powder(s) (embedded within the porous polymer matrix), and residuals of the three solvents (embedded within and on the surface of the porous polymer matrix.

Other powders may be added to the ink in addition to the gelling powder. For example, the ink may contain Hyaluronic Acid (HA) gelling powder and hydroxyapatite (HA) bioceramic to yield a final "HAHA" 3D printed material. The Gelling Powder component will turn into a gel and greatly expand when exposed to water, and the bioceramic particles can remain within the polymer matrix (for example, if they are larger than nano in scale).

In some examples, the powder components of the resulting ink may be comprised of Gelling Powders and electrically conductive materials, such as graphite, graphene, carbon nanotubes, carbon black, micro or nano diamonds—this would impart electrical conductivity to the final fabricated structure. In some examples, the powder components may be comprised of Gelling Powders and biologically derived materials, such as collagens and tissue-specific decellularized extracellular matrices (e.g., muscle, cartilage, kidney, liver, ovary, skin, fat, etc.)—this would impart additional biological properties to the final fabricated structure. In yet other examples, the powder components may be comprised of Gelling Powders, and combination of the previously mentioned types of powders, or any powder compatible with the tri-solvent system. Some ink examples may contain synthetic, natural, hybrid, organic or inorganic nanoparticles (<1 µm) in addition to the Gelling Powders. The Gelling Powder containing inks are highly viscous, but able to flow under their own weight at 1 G. Viscosity may be tailored by altering the amount of evaporant solvent present in the formulation—more for less viscous inks, less for more viscous inks.

As used herein Gelling Powders are distinguished from gels. A Gelling Powder is a highly absorbent solid in powder form. The highly absorbent powder only becomes a gel upon being exposed to, or mixed with, an aqueous solution, as defined below. What distinguishes the present disclosure from prior inks for 3D printing, that may rely on gelling powders, is that the gelling powder in prior inks are mixed with an aqueous solution as a part of the ink and prior to 3D-printing, extruding, or forming the ink to form a hydrogel structure, scaffold, or product. Thereby, the gelling powder of prior inks are, in fact, gels, or in their gel form. In contrast, the Gelling Powder of the present disclosure remains as a Gelling Powder, or solid, within the ink, and through the ink extrusion process, by way of the non-aqueous solvent-based nature of the ink composition. The Gelling Powder of the present disclosure does not become a gel until after 3D printing, extrusion, or forming has been completed and by way of a post-processing treatment. The ink does not comprise a gel. In other words, the Gelling Powder does not become a gel until a post-processing treatment is engaged on the structure, scaffold, or product formed from the ink, such as that described by Approaches 1-3, and the corresponding aqueous based compositions for gelling.

In terms of processing, the bio-compatible polymer is added to and dissolved in the evaporant. Typically, 1 g of polymer is used for every 2-10 g of evaporant (evaporant amount can be changed depending on desired viscosity of final ink). The surfactant and plasticizer are added to the evaporant/dissolved polymer. Amounts relative to evaporant can vary depending on desired final properties of the ink and nature of powder being used. The gelling powder and any other desired powder(s) are added last—typically added such that the gelling powder and make up 85 vol. % or less of the total solids volume of the ink (polymer+powder volume). In some examples, the gelling powder make up 1-85 vol. % of the total solids volume of the ink (polymer+powder volume). In yet other examples, the gelling powder make up 50-85 vol. % of the total solids volume of the ink (polymer+powder volume). This is physically mixed until homogenous at which point it is ready to 3D print via simple room-temperature extrusion.

3D-Printing and Forming

Gelling Powder containing inks are 3D-printed, or otherwise formed, using processes previously described in the '254 patent. In brief, Gelling Powder containing inks are laminarly extruded at room-temperature via pneumatic, piston, or auger driven mechanisms. Within milliseconds after extrusion from fine tipped nozzles (100-1000 µm), the Gelling Powder containing ink solidifies and is capable of supporting its own weight upon deposition onto a substrate while maintaining the Gelling Powders as a solid and not a gel. The substrate may be any material, including previously deposited Gelling Powder containing inks. Through this process, layers of Gelling Powder containing inks can be deposited to created solid structures comprised of fibers (or filaments). Other use of the inks includes extrusion and collection of fibers/filaments. The fibers are flexible and can be used as is or further processed via braiding, cabling, weaving, or other textile methods. Other uses of the inks include casting onto or injecting into a flat, textured, or volumetric mold. Regardless of fabrication method, the resulting Gelling Powder containing structures must be washed to remove residual solvents. Additionally, or alternatively, the Gelling Powder containing inks is further incompatible with any process that requires significant thermal energy additions such as, for example, heating, melting, or the like as the dried gelling powder material would likely degrade.

The resulting 3D printed structures are comprised of: The polymer (exists as nano- and micro-porous matrix, or mesh, in addition to the larger 3D printed macro form); the powder(s)—embedded within the porous polymer matrix, or mesh; residuals of the three solvents—embedded within and on the surface of the porous polymer matrix, or mesh. As used herein, "embedded" or "embedded within" is defined as being integrated into the microstructure of a material or being micro structurally, or physically, anchored.

Residuals of the solvents may be removed via an alternating series of alcohol solution and water washes or through washing in only an alcohol solution. In the alternating series of alcohol solution and water wash example, exposure to water (or majority water solution) will initiate activation and gelation of the Gelling Powder component prior to the drying step. After drying, the structure may be rehydrated upon exposure to sufficient liquid. In the alcohol solution only washing example, activation and gelation does not occur before the drying step. After drying, when pre-activation of the Gelling Powders is desired, exposure to water (or majority water solution or liquid/water environment) would cause the Gelling Powder (embedded within the polymer component) to gel. Comparatively, washing may be carried out in majority alcohol solutions when activation/gelling before drying is to be avoided.

Post-3D-Printing and Forming Processing

Post-forming, Gelling Powder containing structures, or structures formed from an ink where the Gelling Powder is maintained as a gelling powder, or a solid, and not a gel, must be washed and dried.

Figure 2A:
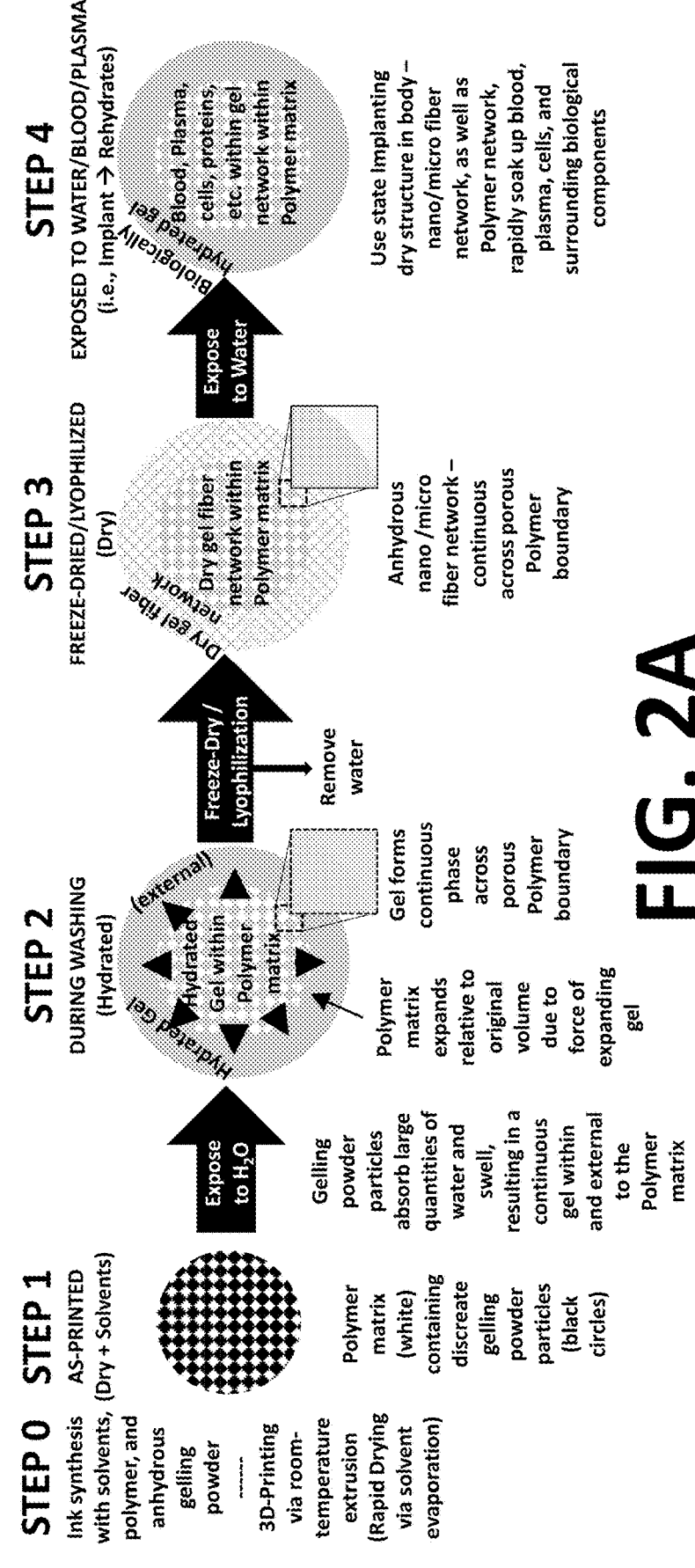
FIG. 2A is a flow diagram of a self-gelling approach (referred to herein as APPROACH 1) of forming a biocompatible polymer matrix, or mesh, which defines a structure of an object that is further encapsulated within a gel that is a product of an ink composition comprising a gelling powder having been washed through a repeated series of alcohol solution, water washes performed after extruding where, due to the highly absorbent nature of the gelling powder, the washing approach will result in the gelling powder absorbing water and gelling to provide the biocompatible polymer matrix, or mesh, structure encapsulated within the gel after extruding, in accordance with an example of the disclosure.
Figure 2B:
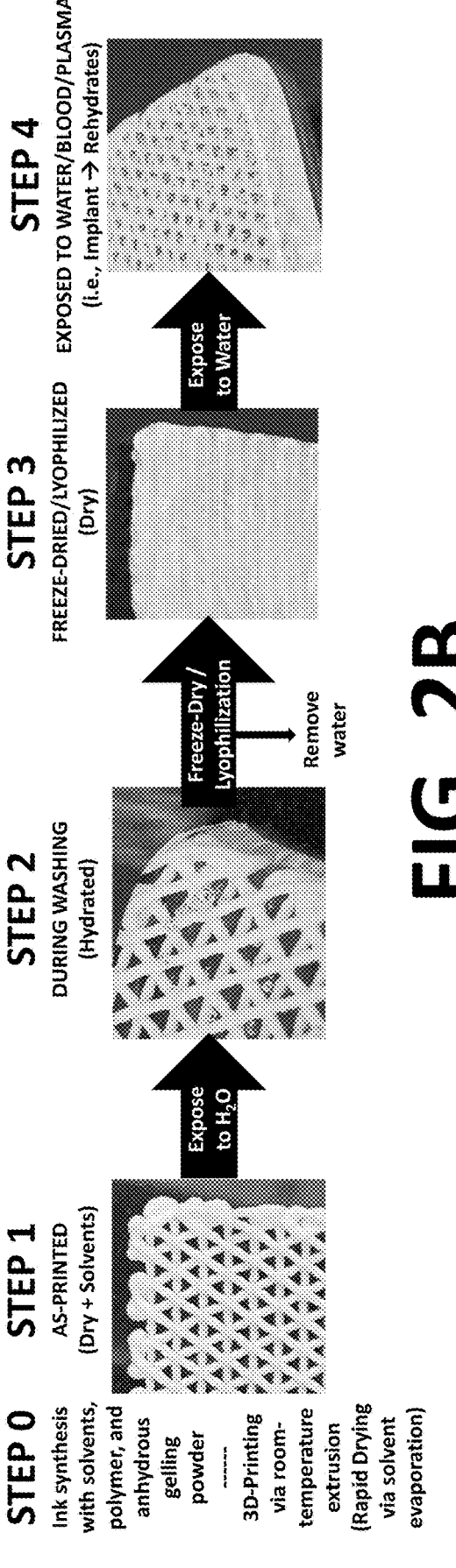
FIG. 2B illustrates images of a product corresponding to the steps of the flow diagram of FIG. 2A for a self-gelling approach (referred to herein as APPROACH 1). The representative products of the images are of the self-gelling approach of forming a biocompatible polymer matrix, or mesh, which defines a structure of an object that is further encapsulated within a gel that is a product of an ink composition comprising a gelling powder having been washed through a repeated series of alcohol solution, water washes performed after extruding where, due to the highly absorbent nature of the gelling powder, the washing approach will result in the gelling powder absorbing water and gelling to provide the biocompatible polymer matrix, or mesh, structure encapsulated within the gel after extruding, in accordance with an example of the disclosure.

Approach 1 (See FIGS. 2A-2B)

As illustrated by the steps of FIG. 2A, and the products illustrated by FIG. 2B corresponding to the respective steps of FIG. 2A, Gelling Powder structures may be washed through a repeating series of alcohol solution, water washes. The alcohol and water washes are provided to remove residual solvents (manufacturing residuals) from the structure. Due to the highly absorbent nature of the Gelling Powder, this washing approach will result in the Gelling Powder being activated by absorbing water and gelling—resulting in biocompatible polymer matrix, or mesh, defining the overall structure of the object, encapsulated within and permeated by a gel. The drying step after washing places the material, or structure of the object, into a shelf-stable form. As used herein "shelf-stable" is defined as being dry, dehydrated, or dried to form a material that may be cut, trimmed, compressed, delivered via cannula, etc., for example, prior to hydration, or subsequent processing. In other words, a shelf-stable structure is capable of being placed and hydrated with surrounding blood, media, plasma, etc. upon implantation—greatly increasing the device's ability to integrate and heal surrounding tissue (distinct from injection of an already hydrated gel, which is much slower to absorb surrounding biological components because it is already hydrated). A final hydration step as outlined by the AQUEOUS-BASED COMPOSITIONS FOR GELLING, below, is provided as the final use processing of the material, or structure of the object.

Figure 3A:
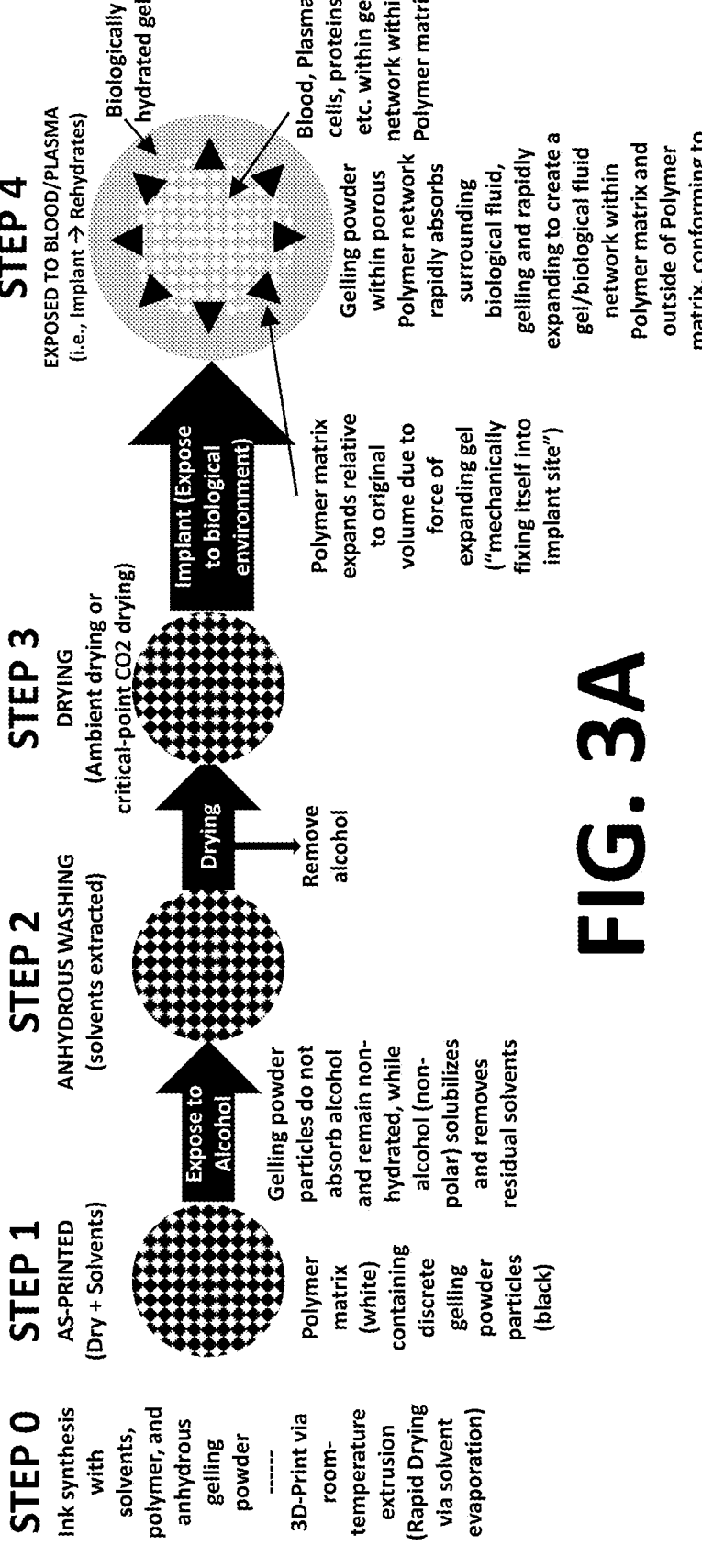
FIG. 3A is a flow diagram of another approach (referred to herein as APPROACH 2) of forming a biocompatible polymer matrix, or mesh, which defines a structure of an object that is further encapsulated within a gel that is a product of a gelling powder comprising an ink composition having been washed through an anhydrous washing conducted in a fully or primarily (>50%) non-aqueous solvent, such as isopropanol, ethanol, or other alcohol-based solution to prevent pre-gelling to provide a lyophilized (freeze-dried) gelling powder that may, thereafter, be relied on in a product that may gel upon rehydration in a controlled environment to provide the biocompatible polymer matrix, or mesh, structure encapsulated within the gel, in accordance with an example of the disclosure.
Figure 3B:
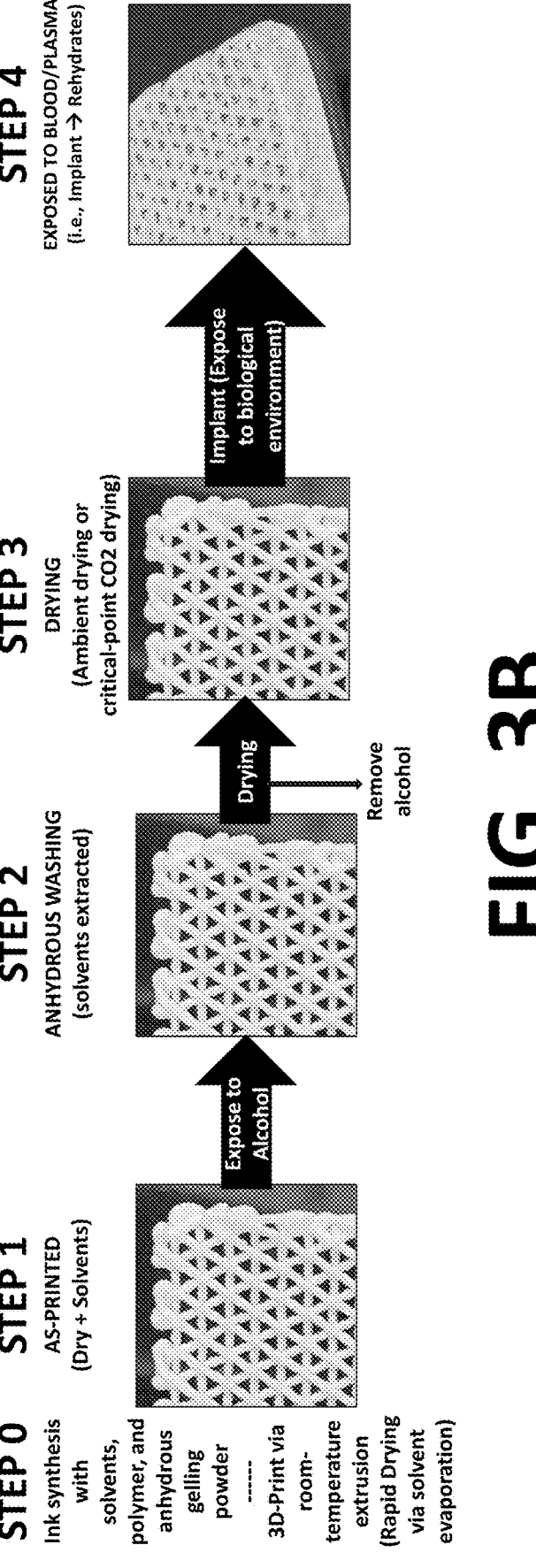
FIG. 3B illustrates images of a product corresponding to the steps of the flow diagram of FIG. 3A (referred to herein as APPROACH 2). The representative products of the images illustrate the forming of a biocompatible polymer matrix, or mesh, which defines a structure of an object that is further encapsulated within a gel that is a product of a gelling powder comprising an ink composition having been washed through an anhydrous washing conducted in a fully or primarily (>50%) non-aqueous solvent, such as isopropanol, ethanol, or other alcohol-based solution to prevent pre-gelling to provide a lyophilized (freeze-dried) gelling powder that may, thereafter, be relied on in a product that may gel upon rehydration in a controlled environment to provide the biocompatible polymer matrix, or mesh, structure encapsulated within the gel, in accordance with an example of the disclosure.
Figures 5A, 5B:
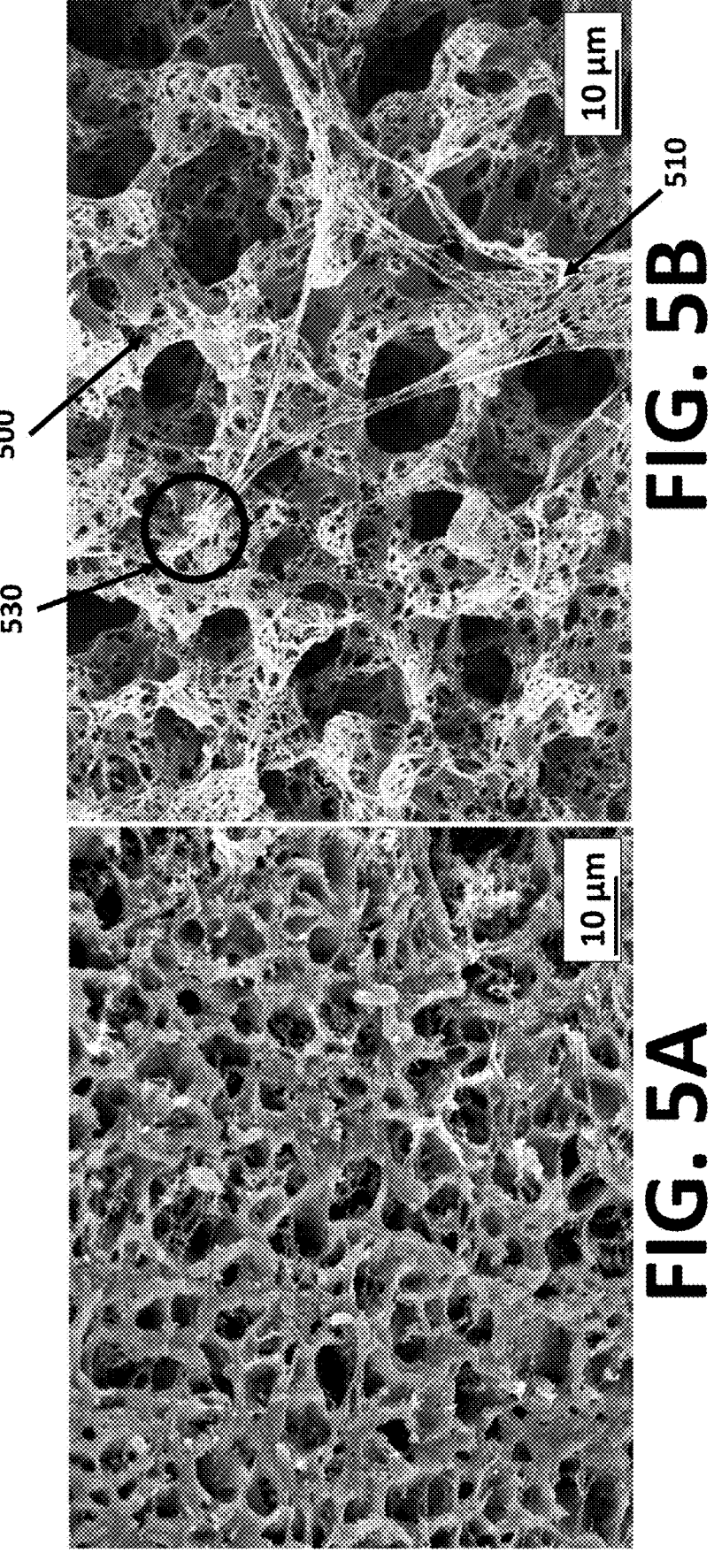
FIG. 5A illustrates an image of a scanning electron micrograph of a 3D printed fiber interior within a larger 3D printed scaffold comprised of gelatin self-gelling powders in a porous matrix before activation/gelation (pre-hydration) (left image), in accordance with an example of the disclosure.
FIG. 5B illustrates an image of a scanning electron micrograph of a 3D printed fiber interior within a larger 3D printed scaffold comprised of gelatin self-gelling powders in a porous matrix after activation/gelation (post-hydration) (right image) wherein the porous microscaffold 500 is labeled, the gelatin gel 510 is labeled, and the gelatin gel anchored within nano- and micro-porous polymer mesh 520 is labeled, in accordance with an example of the disclosure.
Figure 6B:
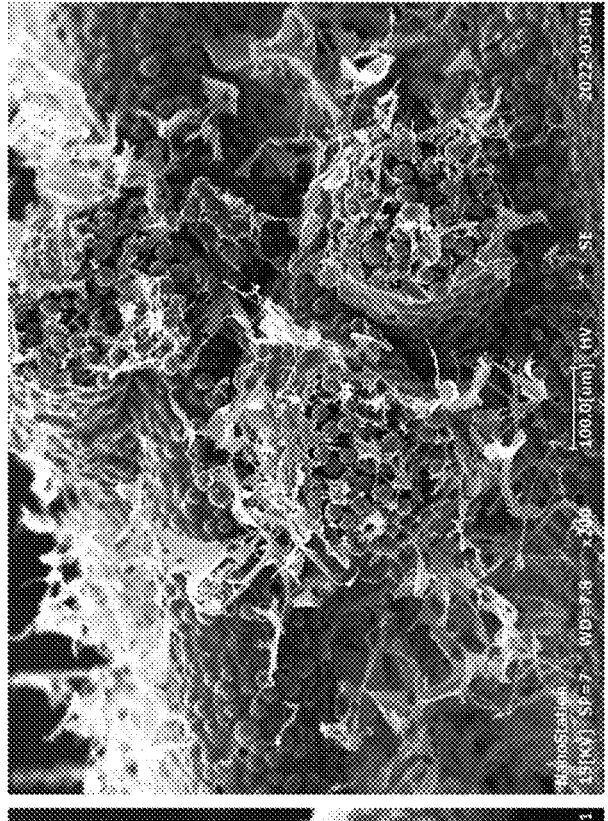
FIG. 6B illustrates an image of a scanning electron micrograph of the cross-sections of a 3D printed fiber interior within a larger 3D printed scaffold comprised of calcium phosphate ceramic spheres and hyaluronic acid self-gelling powders in a porous matrix, or mesh, after activation, or gelation (right image), in accordance with an example of the disclosure.
Figure 6A:
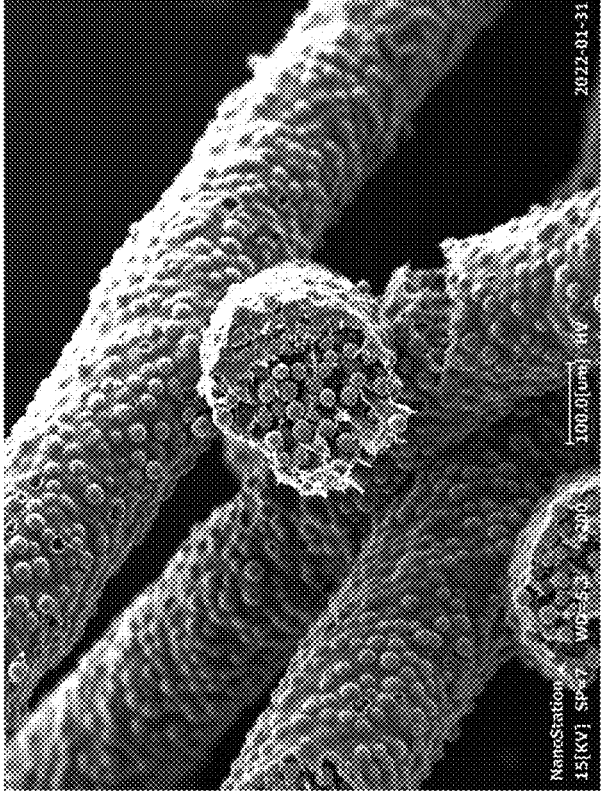
FIG. 6A illustrates an image of a scanning electron micrograph of the cross-sections of a 3D printed fiber interior within a larger 3D printed scaffold comprised of calcium phosphate ceramic spheres and hyaluronic acid self-gelling powders in a porous matrix, or mesh, before activation, or gelation (left image), in accordance with an example of the disclosure.
Figure 7B:
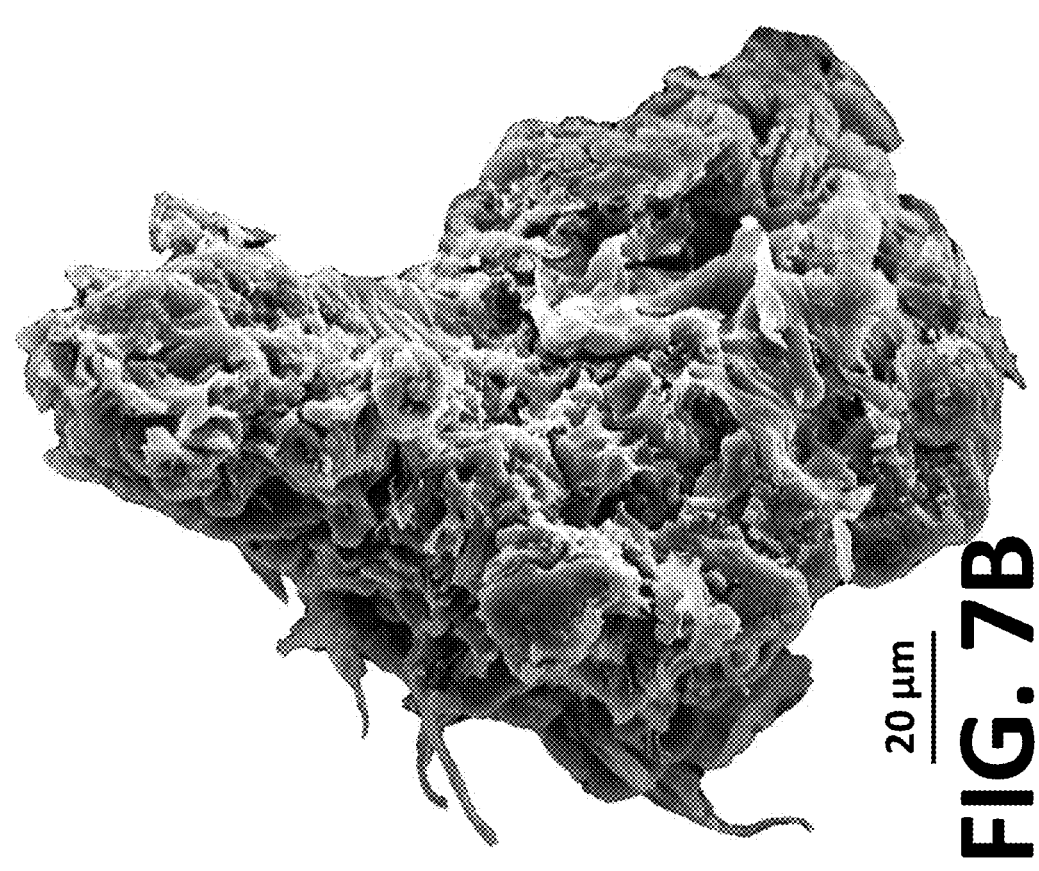
FIGS. 7A-7B illustrate images of scanning electron micrographs (detail) of individual deconstructed scaffold micro-granules obtained via milling of larger 3D printed structures. The left granule of FIG. 7A illustrates an individual deconstructed scaffold micro-granule (non-self-gelling) and, specifically, is comprised of a non- and microporous polylactide-co-glycolide matrix, in accordance with an example of the disclosure. The right granule of FIG. 7B illustrates an individual hyaluronic acid gelling powder containing deconstructed scaffold micro-granule (pre-activation/pre-gelling) and, specifically, is composed of dry hyaluronic acid powder embedded within a nano- and micro-porous PLG matrix, in accordance with an example of the disclosure.
Figure 7A:
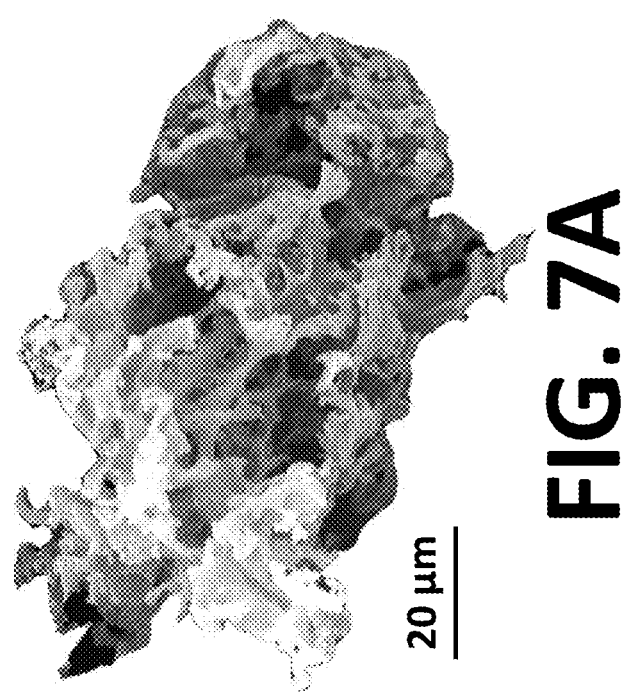
Figures 8A, 8B, 8C:
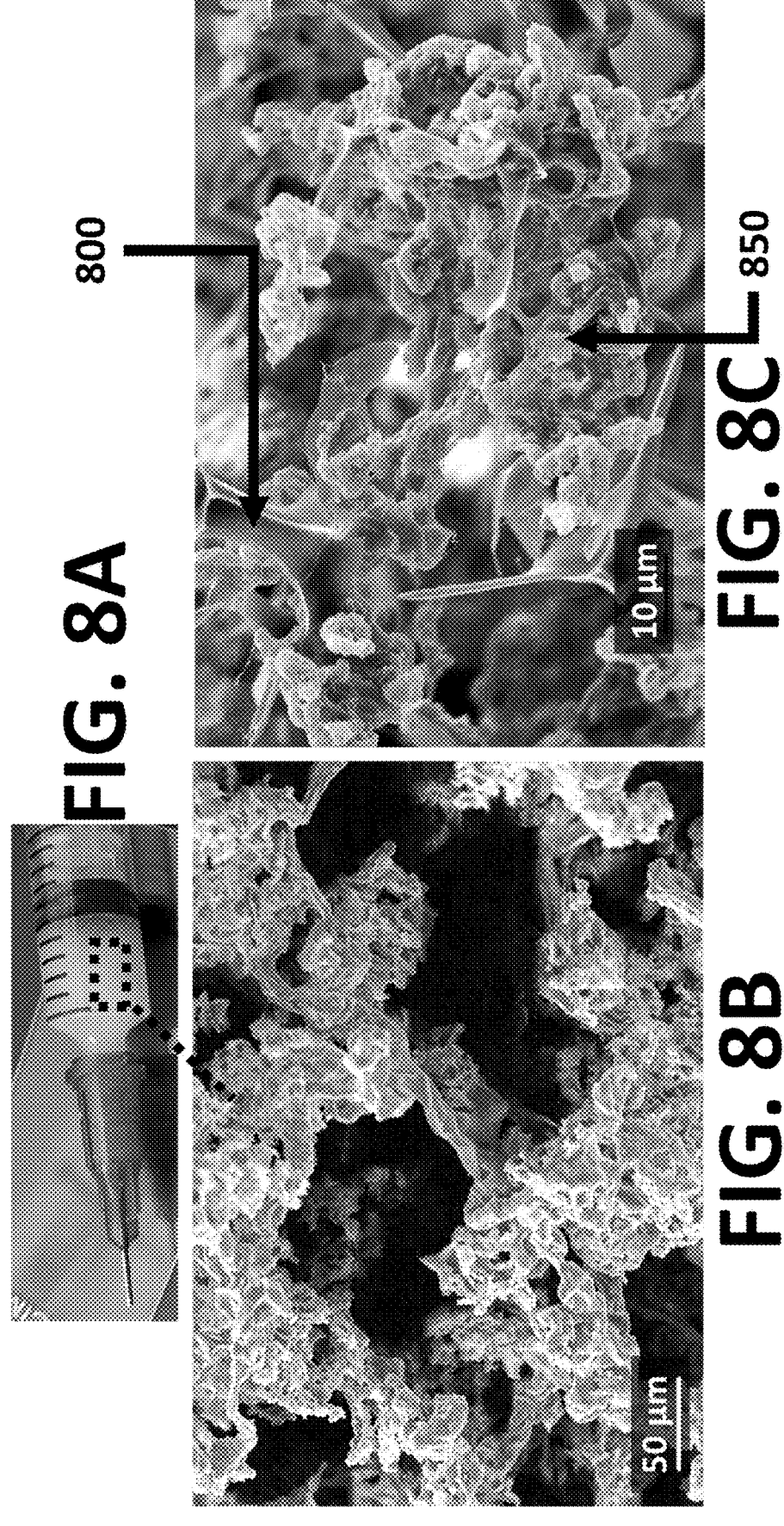
FIG. 8A illustrates a photograph of a syringe (top image) containing a hydrated (saline) mixture of non-self-gelling deconstructed scaffold micro-granules (approximately 33 wt. %) and self-gelling hyaluronic acid deconstructed scaffold micro-granules (approximately 65 wt. %) prior to extrusion through 22 Ga needle wherein the mixture is capable of being extruded through the 22 Ga needle, in accordance with an example of the disclosure.
FIG. 8B illustrates an image of a scanning electron micrograph of extruded micro-granules (left image), in accordance with an example of the disclosure.
FIG. 8C further illustrates an image of a scanning electron micrograph of discrete micro-granules interlocked with each-other and connected via exuded gel wherein gel originating from within the polymer matrix granules 800 are labeled and biocompatible polymer matrix micro-granule from deconstructed scaffold 850 are labeled (right image), in accordance with an example of the disclosure.

Approach 2 (See FIGS. 3A-3B)

Due to the highly absorbent (aqueous) nature of the Gelling Powder materials, washing may be conducted in a fully or primarily (>50%) non-aqueous solvent, such as isopropanol, ethanol, or other alcohol-based solutions in order to prevent pre-gelling if desired, as illustrated by the steps of FIG. 3A, and the products illustrated by FIG. 3B corresponding to the respective steps of FIG. 3A. In other words, the Gelling Powder structure is not washed using an aqueous or primarily aqueous solution (e.g., water) but, instead, is washed using a non-aqueous solvent to prevent activation of the Gelling Powder. In contrast, if exposed to an aqueous or primarily aqueous solution, the structure will gel as it does under APPROACH 1, above. This approach imparts a substantial modification to the ink composition of the '254 patent which requires the structures to otherwise be exposed to water.

Under either approach, washing times and volume of wash media will vary depending on the size and exposed surface area of the object being washed. Typically wash times range from 5-120 minutes. Multiple wash cycles may be used. Post-washing drying can be achieved through any single or combination of multiple means. In one example, the Gelling Powder structure, or Gelling Powder containing object, that has been washed in primarily alcohol solution can be air dried or dried with flowing air (fan, compressed air, etc.) assistance. In another example, the Gelling Powder structure, or Gelling Powder containing object, that has been washed in primarily alcohol solution can be lyophilized (freeze-dried). However, due to the high alcohol content, the user must ensure that the lyophilizer used is capable of condensing (freezing) the solution used to wash the Gelling Powder structure, or Gelling Powder containing object. In another example, the Gelling Powder structure, or Gelling Powder containing object, that has been washed in alcohol solution can be critically point dried using super critical $CO_2$ at appropriate pressures and temperatures. It is critical that any object going through critical point drying be substantially free of water prior to critical point drying. The resulting dried, Gelling Powder structure, or Gelling Powder containing object, should be shelf stable as long as it is stored in a moisture free environment (desiccator, hermetically sealed packaging, etc.) at temperatures typically lower than 60° Celsius. The resulting dried, Gelling Powder, or Gelling Powder containing object, can be described as a composite of biocompatible polymer and distinct particles of embedded Gelling Powder. The biocompatible polymer component is typically microporous, and could be described as a disordered, interconnected mesh network. Within the mesh network, Gelling Powder particles are trapped, and the fabricated structures do not contain any gel or substantial amount of moisture (e.g., they are solid materials, not gel or liquid). Thereafter, the Gelling Powder particles may be activated, or hydrated, as outlined by the AQUEOUS-BASED COMPOSITIONS FOR GELLING, below.

With respect to APPROACHES 1-2, above, dry Gelling Powders may be used with and/or 3D printed into additionally distinct material/structures such as those described in: U.S. Pat. No. 9,327,448 entitled METHODS FOR FABRICATING THREE-DIMENSIONAL METALLIC OBJECTS VIA ADDITIVE MANUFACTURING USING METAL OXIDE PASTES, filed 1 Aug. 2014; U.S. Pat. No. 10,236, 528 entitled THREE DIMENSIONAL EXTRUSION PRINTED ELECTROCHEMICAL DEVICES, filed 18 Jul. 2016; U.S. Pat. No. 10,350,329 entitled GRAPHENE-BASED INK COMPOSITIONS FOR THREE-DIMENSIONAL PRINTING APPLICATIONS, filed 15 Oct. 2015; U.S. Pat. No. 10,793,733 entitled INK COMPOSITIONS FOR FABRICATING OBJECTS FROM REGOLITHS AND METHODS OF FORMING THE OBJECTS, filed 7 Apr. 2016; U.S. Patent Publication No. 2019/0343989 A1 entitled SURGICALLY-FRIENDLY TISSUE PAPERS FROM ORGAN-SPECIFIC DECELLULARIZED EXTRACELLULAR MATRICES, filed 16 May 2019; and U.S. Patent Publication No. 2020/0353129 A1 entitled WATER-SOLUBLE SALT PARTICLE CONTAINING COMPOSITIONS AND POROUS MATERIALS MADE THEREFROM, filed 29 Apr. 2020; all of which are herein incorporated by reference in their entirety.

Approach 3 (See FIG. 4)

Dried Gelling Powder Structures, or Gelling Powder containing structures, such as extruded fibers, can undergo additional processing to yield gelling powder containing, deconstructed scaffold micro-granules or, in other words, Deconstructed Scaffold Gelling Granules. Specifically, dry Gelling Powder Structures, or Gelling Powder containing structures, can be mechanically milled (cutting mill) and sieved to yield powders with individual particle composition and microstructure representative of a larger 3D printed or otherwise formed Gelling Powder Structure, or Gelling Powder containing structure. Such a collection of gelling powder containing, deconstructed scaffold micro-granule powders would be shelf-stable in dry form, but could be hydrated (see below), resulting in gelling of the powders contained within the particles' polymer matrices lubricating the particles, and create an interconnected network of discrete microgranules connected by and suspended within a gel network that is capable of extrusion through a syringe. Such a hydrated material could be 3D printed into an additionally distinct material/structure (one comprised of non-continuous distinct units of nano- and micro-porous biocompatible polymer particles, connected by a gel network characterized by microstructured anchored "points" within each biocompatible polymer microparticle). The term "Deconstructed Scaffold Gelling Granules", as defined herein, refers to the product resulting from milling, not before. In other words, 3D printed, extruded or otherwise formed products may be additionally milled to yield powders, with each powder particle having a composition and microstructure representative of the pre-milled material. The Deconstructed Scaffold Gelling Granules are those structures created from those powders yielded from the milled extruded, or otherwise formed, products Milling a large volume of material makes powders from that material and each powder particle is, essentially, a tiny version of that larger structure which was milled. Thereby, each particle contains a composite of some gelling powder, polymer, and any other powder that may have been in the original material or ink. Further, milled powders may also be sieved and sorted to obtain specific size ranges if desired. Micro-granules are typically greater than 20 μm in size. In one particular example, for cell delivery and tissue repair applications, it may be important that the micro-granules be several times larger than the majority of the immediately adjacent or adherent cells. This size difference promotes interaction of individual cells with individual micro-granules in a manner similar to individual cells interacting with a much larger structure comprised of the same material and defined by the same microstructure as the micro-granules.

APPROACH 3 is further illustrated by FIG. 4. In FIG. 4, a 3D printed structure comprising a dry gelling powder embedded within a porous polymer matrix, or mesh, structure, as formed by either APPROACH 1 or 2 above (Step 1 of FIG. 4), may be mechanically milled to form shelf-stable Deconstructed Scaffold Gelling Granule which are representative of the components of the original larger structure (Step 2 of FIG. 4). The mechanically milled Deconstructed Scaffold Gelling Granules may be combined with an aqueous solution (e.g., blood, water, etc.), thereby, activating/gelling the Gelling Powder component of the Deconstructed Scaffold Gelling Granules to form an activated/gelled scaffold suspension of the Deconstructed Scaffold Gelling Granules (Step 3 of FIG. 4). The micro-granule particles of the scaffold suspension of the Deconstructed Scaffold Gelling Granules are anchored, yet also a flowable, gel-particle suspension upon gelation. The suspension may be loaded into a syringe and injected into or onto a site such as, for example, tissue, organ, or wound site (Step 4 of FIG. 4). Accordingly, the Deconstructed Scaffold Gelling Granules may be further utilized as a gelling powder of either APPROACH 1 and 2.

As used herein in view of the above approaches, the washed structure is dried to obtain its "shelf-stable" state. Drying may be done via any number of methods, including: Air drying (with or without aid, such as a fan); critical point drying; lyophilization. The dried structure may now be comprised only of, consist of, or consist essentially of the nano- and micro-porous polymer matrix, or mesh, with embedded Gelling Powders and/or Deconstructed Scaffold Gelling Granules (and other powders if they were added). The dry structures may be flexible and are capable of being cut with a scissors, razor blade, or equivalent sharp tool. The dry structures may also be capable of holding a suture or a thread. The dry structures, when in thin (sheet or membrane-like form) may also be compressed and pushed down a cannula.

As also used herein in view of the above approaches, upon exposure to sufficient water, the Gelling Powders and/or the Deconstructed Scaffold Granules, within the polymer matrix, or mesh, "activates"—essentially soaking up more than 5 times its own weight in water (and whatever is in the water . . . i.e., blood). The absorption results in a very large volume change and effective transformation of dry solid gelling powder particles into expansive, wet hydrogel that saturates the nano- and micro-pores of the polymer (i.e., polyester) matrix, or mesh, and ends up exuding beyond the boundaries of the polymer component, encapsulating polymer material and generally encapsulating the larger 3D printed structure.

Aqueous-Based Compositions for Gelling

Gelling Powder containing washed and dried structures are capable of exuding "microstructurally anchored" or "physically anchored" gel upon exposure to aqueous based liquids, as illustrated by both FIGS. 2A, 2B, 3A, and 3B. Essentially, the distinct, dry Gelling Powders and/or Deconstructed Scaffold Gelling Granules, within the biocompatible polymer matrix, or mesh, absorb the water (and anything within the water) and begin expanding as they transform into a hydrogel (mostly water containing material, with a minority, interconnected solid polymer network—"mostly" being defined as >50% by volume). This process is referred to, herein, as "activation" of the Gelling Powders and/or Deconstructed Scaffold Gelling Granules. This expansion results in pressure on the surrounding biocompatible polymer matrix, or mesh, network, and exuding or expulsion of the now interconnected gel network from the still solid, highly porous, biocompatible polymer network. As a result of the expanding gel pressure on the encompassing biocompatible polymer, solid mesh network, the mesh network expands, resulting in a macroscopic expansion of the fabricated object (typically, 0.5 to 20% linear expansion in all directions). The gel volume increases to such a degree as a result of exposure to an aqueous based solution that the gel network exudes beyond the boundaries/radius of printed, or otherwise formed, biocompatible polymer mesh network—resulting in a structure that can be described as a highly porous, but solid, polymer mesh network embedded within a gel. Importantly, the polymer mesh network is not only embedded within the gel, but the gel is embedded within the polymer mesh network (e.g., the nano- and micro-pores of the polymer network). This has important implications for properties and use, as the gel is microstructurally, or physically, anchored to/within the structural, porous biocompatible polymer component. Upon activation, the post-processing treatment of transitioning the Gelling Powder and/or Deconstructed Scaffold Gelling Granule to a gel exuded from within the material, or structure, (i.e., inside out gelation). This is in contrast to adding a gel to or adhering a gel to an existing surface (i.e., outside in) such as that taught by U.S. Publication No. 2019/0060516 which adds a gel to an existing surface. It has been found that gels that are independent of a structure shear and migrate, or move. In contrast, the activated gels of the present disclosure which are anchored in the structure, scaffold, or product, as described herein, do not shear or migrate or do not shear or migrate to such a degree. In other words, the gels, which exude from within the material, or structure, have an anchor point as opposed to those gels which are added to a pre-existing material, or structure such that if a shear force is applied to the gel that is exuding from the nano- and micro-porous polymer matrix, or mesh, and then released, the gel moves back to its original position (like it is stuck or anchored within the more substantial nano- and micro-porous polymer matrix, or mesh). This limits gel migration and increases residence time of the gel when it is implanted in this 3D printed form, relative to the gel just being injected or the gel being subsequently added to an existing (3D printed or not) structure.

In another example of the present disclosure, the previously described inks with a powder component may be a combination of one or more of Gelling Powder, Deconstructed Scaffold Gelling Granule, micro-scale (1-100 micrometer on average) non-gelling powder particles, and nano-scale (0.001 to 0.999 micrometer on average) non-gelling particles. The micro-particles may be comprised of any material that is not substantially soluble, or insoluble, in dichloromethane, including but not limited to: ceramics, metals, alloys, covalent solids, biological particles (extracellular matrix, collagens, proteins), or modified particles thereof. Modifications may include, but are not limited to, surface functionalization, coating, and encapsulation with other materials. The nano-scale particles maybe include similar categories of materials of the micro-scale particles, in addition to proteins, drugs, peptides, bioactive factors.

The dry Gelling Powder and/or Deconstructed Scaffold Gelling Granule containing structure can be hydrated/gelled with any number of aqueous based solutions. This includes but is not limited to the following: water, saline, blood, blood plasma, refined blood products (platelet rich plasmas), water-based solutions containing cells, drugs, proteins, peptides, cell or tissue culture media, small molecules, nanoparticles, antibiotics, antimycotics, etc. The rate of hydration and degree of gelation (i.e., how much gel is exuded from the polymer network) depends on multiple factors including but not limited to: relatively vol. % Gelling Powder and/or Deconstructed Scaffold Gelling Granule in structure (relative to other powders as well as to the polymer component), molecular weight and polydispersity of the Gelling Powder and/or Deconstructed Scaffold Gelling Granule material, aqueous solution used for gelation. In this way, gelation can be controlled to regulate the gel "radius" around the biocompatible polymer fibers or large structures (i.e., small amounts of Gelling Powder and/or Deconstructed Scaffold Gelling Granule could result in a gelling radius around the printed fibers of ~10-100 μm or extend several millimeters).

The dry Gelling Powder and/or Deconstructed Scaffold Gelling Granule containing structures are typically flexible, depending on the form factor, and can be elastically and plastically deformed (bent, folded, etc.), cut, stamped, and otherwise trimmed to shape. These processes can also be performed after the structure has been hydrated and gelled.

Hydrated and gelled structures can optionally be lyophilized (freeze dried), resulting in a moisture free structure defined by the original biocompatible polymer mesh network embedded within a dried gel network (and the dried gel network also inside the polymer mesh microstructure).

While this invention has been described with reference to examples thereof, it shall be understood that such description is by way of illustration only and should not be construed as limiting the scope of the claimed examples. Accordingly, the scope and content of the examples are to be defined only by the terms of the following claims. Furthermore, it is understood that the features of any example discussed herein may be combined with one or more features of any one or more examples otherwise discussed or contemplated herein unless otherwise stated.

What is claimed is:

1. A 3D printed structure having one or more self-gelling components, the 3D printed structure comprising:
   a dry gelling powder embedded and encapsulated within a microstructure of a porous polymer matrix structure, the dry gelling powder configured to form a gel when contacted with an aqueous solution causing it to gel and encapsulate the porous polymer matrix structure;
   wherein the polymer matrix structure is a non-aqueous solvent based polymer matrix structure.

2. The structure of claim 1, further comprising micro and nano particles embedded within the porous polymer matrix structure, wherein the micro and nano particles are one or more of electrically conductive materials, ceramic materials, metallic materials, and biologically derived materials.

3. The structure of claim 1, wherein the polymer matrix structure comprises a biocompatible polymer.

4. The structure of claim 3, wherein the gel is physically anchored within the microstructure of the biocompatible polymer matrix structure.

5. A 3D printed structure having one or more self-gelling components, the 3D printed structure comprising:
   a polymer matrix structure comprising a microstructure encapsulating, or integrating, an anhydrous washed and absorbent dry gelling powder of discreate, dry particles that are configured to form a gel in an aqueous based solution and encapsulate the porous polymer matrix structure;
   wherein the polymer matrix structure is a non-aqueous solvent based polymer matrix structure.

6. The structure of claim 5, wherein the gel from the gelling powder is configured to be anchored within the microstructure of the polymer matrix structure upon gelation.

7. The structure of claim 5, further comprising a network of micro and nano particles configured to be embedded within the porous polymer matrix structure by being encapsulated in a solid-gel suspension encapsulated, or integrated, within the polymer matrix structure upon gelation.

8. The structure of claim 5, wherein the polymer matrix structure comprises a biocompatible polymer.

9. The structure of claim 5, wherein the structure is not and does not comprise a gel.

* * * * *